United States Patent [19]

Kirst et al.

[11] 4,452,784
[45] Jun. 5, 1984

[54] C-23-MODIFIED DERIVATIVES OF DMT

[75] Inventors: Herbert A. Kirst; John E. Toth, both of Indianapolis, Ind.

[73] Assignee: Eli Lilly and Company, Indianapolis, Ind.

[21] Appl. No.: 399,656

[22] Filed: Jul. 19, 1982

[51] Int. Cl.$^3$ .................. A61K 31/70; C07H 17/08
[52] U.S. Cl. ............................ 424/180; 424/181; 536/7.1
[58] Field of Search ................. 536/7.1; 424/180, 181

[56] References Cited

U.S. PATENT DOCUMENTS

| | | | |
|---|---|---|---|
| 3,459,853 | 8/1969 | Gorman et al. | 424/121 |
| 4,304,856 | 12/1981 | Baltz et al. | 536/7.1 |
| 4,321,361 | 3/1982 | Baltz et al. | 536/17 R |
| 4,321,362 | 3/1982 | Baltz et al. | 536/17 R |
| 4,341,770 | 7/1982 | Ose et al. | 424/181 |
| 4,341,771 | 7/1982 | Kirst et al. | 424/181 |
| 4,358,584 | 11/1982 | Nash et al. | 536/7.1 |

FOREIGN PATENT DOCUMENTS 56-122397 9/1981 Japan .
2081711 2/1982 United Kingdom .

OTHER PUBLICATIONS

Tanaka et al., "Synthesis of 4'-Deoxymycaminosyl Tylonolide," *J. Antibiotics* 34 (10), 1374–1376 (1981).
Tanaka et al., "Synthesis of Derivatives of 4'-Deoxymycaminosyl Tylonolide and Mycaminosyl Tylonolide Modified at C-23," Ibid 34 (10), 1377–1380 (1981).
Tanaka et al., "Syntheses of 23-Dialkylamino Derivatives of Mycaminosyl Tylonolide and 4'-Deoxymycaminosyl Tylonolide Effective Against Gram-Negative Bacteria," Ibid 35 (1), 113–116 (1982).
S. Omura, "Biosynthesis of 16-Membered Macrolide Antibiotics," Japan Antibiotic Research Association 224th Scientific Meeting, May 22, 1981 (notes from talk).
Derwent Abstract No. 12994E of Japanese Unexamined Patent 7004-999 (ZH Biseibutsu Kagaku Ken), Jan. 11, 1982.
Derwent Abstract No. 12995E of Japanese Unexamined Patent 7005-000 (ZH Biseibutsu Kagaku Ken), Jan. 11, 1982.
Derwent Abstract No. 60702D/34 of European Patent 33-433 (Schering Corp.) Nov. 9, 1979.
Tanaka et al., "Syntheses of Recyclized Macrolide Antibiotics and Related Derivatives from Mycaminosyltylonolide", *Bull. Chem. Soc. Jpn.*, 54, 3837–3845 (1981).
Matsubara et al., "Chemical Transformation of Tylosin, a 16-Membered Macrolide, and Its Structure-Activity Relationship", *Chem. Pharm. Bull.* 30 (1), 97–110 (1982).

*Primary Examiner*—Johnnie R. Brown
*Attorney, Agent, or Firm*—Nancy J. Harrison; Arthur R. Whale

[57] ABSTRACT

C-23-Modified derivatives of demycinosyltylosin (DMT) of the formula:

[Chemical structure 1]

wherein
R is iodo, bromo, chloro, fluoro, —S—$R^4$, azido, —$NHR^5$, pyridinium or —$OSO_2CF_3$;

$R^1$ is hydrogen, optionally substituted $C_1$-$C_5$-alkanoyl or optionally substituted benzoyl, phenylacetyl, phenylpropionyl, phenoxyacetyl or phenylthioacetyl;

$R^2$ is hydrogen, optionally substituted $C_1$-$C_5$-alkanoyl or optionally substituted benzoyl, phenylacetyl or phenylpropionyl;

$R^3$ is hydrogen, optionally substituted $C_1$-$C_5$-alkanoyl or optionally substituted benzoyl, phenylacetyl or phenoxyacetyl;

$R^4$ is hydrogen, optionally substituted $C_1$-$C_6$-alkyl, cyclohexyl, $C_1$-$C_5$-alkanoyl, optionally substituted phenyl or benzyl, or an optionally substituted heteroaryl group selected from imidazolyl, pyrazolyl, pyridyl, pyrimidyl, pyrazinyl, pyridazinyl, triazinyl, triazolyl, tetrazolyl, oxazolyl, isoxazolyl, oxadiazolyl, thiazolyl, isothiazolyl, thiadiazolyl, thienyl and furanyl; and $R^5$ is hydrogen or an acyl group selected from optionally substituted $C_1$-$C_5$-alkanoyl or optionally substituted benzoyl, phenylacetyl or phenylpropionyl;

and salts thereof are useful antibiotics or intermediates to antibiotics.

35 Claims, No Drawings

C-23-MODIFIED DERIVATIVES OF DMT

SUMMARY OF THE INVENTION

This invention relates to C-23-modified derivatives of demycinosyltylosin (DMT) having formula 1:

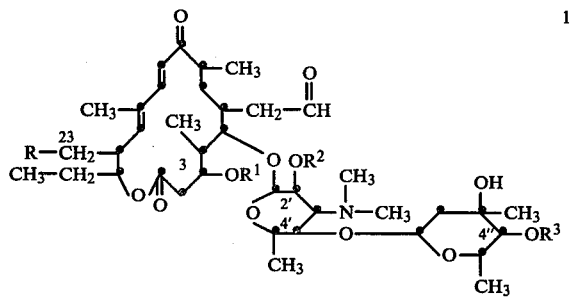

wherein

R is iodo, bromo, chloro, fluoro, —S—$R^4$, azido, —$NHR^5$, pyridinium or —$OSO_2CF_3$;

$R^1$ is hydrogen, optionally substituted $C_1$-$C_5$-alkanoyl or optionally substituted benzoyl, phenylacetyl, phenylpropionyl, phenoxyacetyl or phenylthioacetyl;

$R^2$ is hydrogen, optionally substituted $C_1$-$C_5$-alkanoyl or optionally substituted benzoyl, phenylacetyl or phenylpropionyl;

$R^3$ is hydrogen, optionally substituted $C_1$-$C_5$-alkanoyl or optionally substituted benzoyl, phenylacetyl or phenoxyacetyl;

$R^4$ is hydrogen, optionally substituted $C_1$-$C_6$-alkyl, cyclohexyl, $C_1$-$C_5$-alkanoyl, optionally substituted phenyl or benzyl, or an optionally substituted heteroaryl group selected from imidazolyl, pyrazolyl, pyridyl, pyrimidyl, pyrazinyl, pyridazinyl, triazinyl, triazolyl, tetrazolyl, oxazolyl, isoxazolyl, oxadiazolyl, thiazolyl, isothiazolyl, thiadiazolyl, thienyl and furanyl; and $R^5$ is hydrogen or an acyl group selected from optionally substituted $C_1$-$C_5$-alkanoyl or optionally substituted benzoyl, phenylacetyl or phenylpropionyl;

and to the acid addition salts of these compounds. The compounds of this invention are useful as antibiotics and/or as intermediates to antibiotics. This invention also relates to pharmaceutical compositions comprising these compounds and to methods of treatment wherein these compounds or compositions are administered to obtain an antibiotic effect or to enhance growth promotion in animals.

DETAILED DESCRIPTION OF THE INVENTION

This invention relates to new antibiotics. In particular, this invention relates to C-23-modified derivatives of DMT and to their acid addition salts. This invention also relates to methods of treating certain infections with, methods of promoting growth in animals with, and pharmaceutical compositions comprising the specified derivatives of DMT and their pharmaceutically acceptable acid addition salts.

New, improved antibiotics are continually in demand. In addition to antibiotics which are useful for treating human diseases, improved antibiotics are also needed in the veterinary field. Increased potency, expanded spectrum of bacterial inhibition, increased in vivo efficacy, and improved pharmaceutical properties (such as greater oral absorption, higher blood or tissue concentrations, longer in vivo half life, and more advantageous rate or route of excretion and rate or pattern of metabolism) are some of the goals for improved antibiotics.

DMT is an antibiotic described by Richard H. Baltz, Gene M. Wild, and Eugene T. Seno in U.S. Pat. No. 4,321,361, issued on Mar. 23, 1982. The structure of DMT is shown in formula 2:

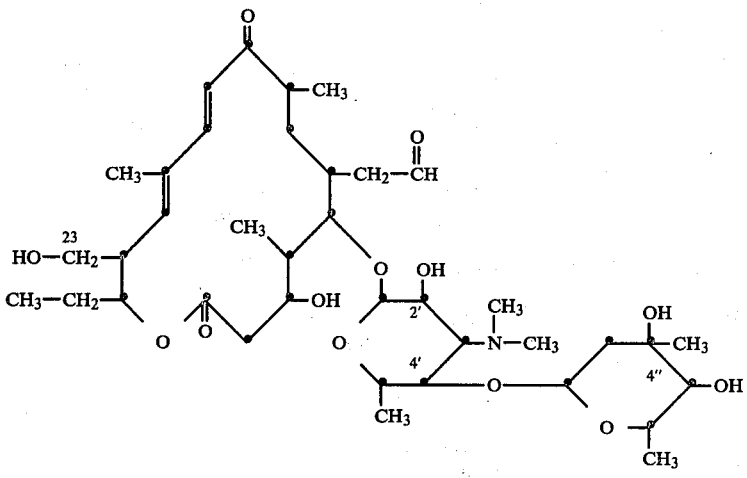

Displacement of the 23-hydroxyl group of DMT provides the derivatives which are the subject of this invention. Displacement is accomplished by converting the 23-hydroxyl group to a suitable leaving group, such as triflate, and then displacing the leaving group with an appropriate nucleophile under suitable conditions. These derivatives have excellent antimicrobial activity against gram-positive bacteria and Mycoplasma species.

The derivatives of DMT of this invention are compounds of formula 1

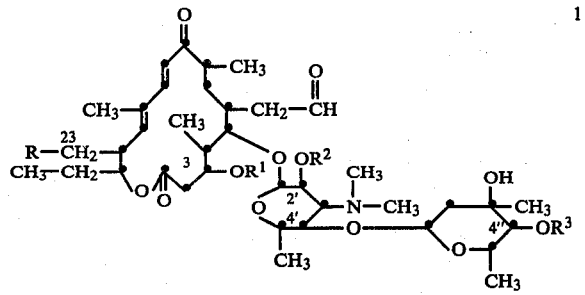

wherein:
- R is iodo, bromo, chloro, fluoro, —S—$R^4$, azido, —$NHR^5$, pyridinium or —$OSO_2CF_3$;
- $R^1$ is hydrogen, optionally substituted $C_1$-$C_5$-alkanoyl or optionally substituted benzoyl, phenylacetyl, phenylpropionyl, phenoxyacetyl or phenylthioacetyl;
- $R^2$ is hydrogen, optionally substituted $C_1$-$C_5$-alkanoyl or optionally substituted benzoyl, phenylacetyl or phenylpropionyl;
- $R^3$ is hydrogen, optionally substituted $C_1$-$C_5$-alkanoyl or optionally substituted benzoyl, phenylacetyl or phenoxyacetyl;
- $R^4$ is hydrogen, optionally substituted $C_1$-$C_6$-alkyl, cyclohexyl, $C_1$-$C_5$-alkanoyl, optionally substituted phenyl or benzyl, or an optionally substituted heteroaryl group selected from imidazolyl, pyrazolyl, pyridyl, pyrimidyl, pyrazinyl, pyridazinyl, triazinyl, triazolyl, tetrazolyl, oxazolyl, isoxazolyl, oxadiazolyl, thiazolyl, isothiazolyl, thiadiazolyl, thienyl and furanyl; and
- $R^5$ is hydrogen or an acyl group selected from optionally substituted $C_1$-$C_5$-alkanoyl or optionally substituted benzoyl, phenylacetyl or phenylpropionyl.

The acid addition salts of these compounds are also part of this invention.

The term "$C_1$-$C_5$-alkanoyl" as used herein means an acyl moiety derived from a carboxylic acid containing from one to five carbon atoms. In such a moiety, the alkyl group can be straight, branched, or cyclic. When optionally substituted, this group can bear one to three halo substituents. Halo substituents are selected from the group consisting of Cl, Br and F. Acetyl, chloroacetyl, trichloroacetyl, trifluoroacetyl, propionyl, n-butyryl, isobutyryl, n-valeryl, and isovaleryl are examples of such groups.

The terms "optionally substituted benzoyl, phenylacetyl, phenylpropionyl, phenoxyacetyl or phenylthioacetyl," "optionally substituted benzoyl, phenylacetyl or phenylpropionyl," "optionally substituted benzoyl, phenylacetyl or phenyoxyacetyl," and "optionally substituted phenyl or benzyl" means that the phenyl portion of the moiety is optionally substituted by from one to five halo or methyl groups or by from one to two methoxyl, nitro or hydroxyl groups.

The term "optionally substituted heteroaryl group" as used herein means that the heteroaryl group may have at least one suitable substituent(s) such as $C_1$-$C_4$-alkyl, methoxy, ethoxy, hydroxy (or the keto tautomer), phenyl or phenyl optionally substituted by one or more halo, methyl or methoxyl groups.

The terms "$C_1$-$C_6$-alkyl" and "$C_1$-$C_4$-alkyl" as used herein mean a straight- or branched-chain alkyl group containing from one to six or one to four carbon atoms, respectively. Such groups include methyl, ethyl, isopropyl, n-butyl, sec-butyl, isobutyl, tertbutyl, and, for the former, n-pentyl, isopentyl, n-hexyl and the like.

The C-23-modified derivatives of DMT of this invention are prepared from DMT. The preparation of DMT is described by Baltz et al. in U.S. Pat. No. 4,321,361.

Preparation of the C-23-modified derivatives of DMT involves two steps. First, the 23-hydroxyl group is converted to a suitable leaving group, such groups being well known in the art. The triflate anion is a preferred leaving group. With very reactive nucleophiles, however, other leaving groups, such as the mesylate anion, the tosylate anion, iodide or bromide may also be suitable.

The second step in the preparation of the DMT derivatives involves displacement of the leaving group by the appropriate nucleophile under suitable conditions which are well exemplified in the art of displacement reactions.

The C-23 derivatives wherein R is —$NHR^5$ are prepared via the 23-azido derivative (R=$N_3$). The 23-azido derivative is first reduced to the 23-amino derivative; triphenylphosphine in aqueous tetrahydrofuran (THF) is an example of suitable reducing agent for this purpose. The 23-amino derivative can then be selectively acylated on the amino group, using standard acylation procedures, to give those DMT derivatives wherein $R^5$ is an acyl group.

The 23-O-triflate is preferably prepared by a method analogous to that described in our co-pending application entitled METHOD OF PREPARING 23-MONO-ESTERS OF OMT AND DMT, serial No. 330,295, filed Dec. 14, 1981, now abandoned, which is incorporated herein by reference. Using this procedure, the 23-O-triflate of DMT can be prepared without concomitant reactions at the other hydroxyl groups which are present. A similar reaction can be used to prepare the corresponding mesylate or tosylate directly.

When triflate is used as the leaving group, it is not necessary to isolate the intermediate triflate derivative; displacement with the appropriate nucleophile can be carred out in situ. When less reactive leaving groups are used, the intermediate is sufficiently stable and may be isolated prior to the displacement reaction if so desired.

The C-23-modified derivatives of this invention wherein $R^1$, $R^2$, or $R^3$ are other than hydrogen (the ester derivatives) are prepared by esterifying the corresponding C-23-modified DMT derivative on the 2', 4", and/or 3-hydroxyl groups by treatment with acylating agents, using standard methods well exemplified in the art. The preparation of 2'-O-ester derivatives of C-23-modified derivatives of DMT is accomplished by procedures similar to those described by Baltz et al. in U.S. Pat. Nos. 4,321,361 and 4,321,362. 4"- and 3-Ester derivatives of C-23-modified derivatives of DMT may be prepared by acylation of the 4"- and 3-hydroxyl groups as described by Herbert A. Kirst in a co-pending application entitled 4"- AND 3-ESTER DERIVATIVES OF DMT AND DMOT, serial No. 354,262, filed Mar. 3, 1982, which is incorporated herein by reference.

Esters of those C-23 derivatives wherein R is iodo, bromo, fluoro, chloro, —S—$R^4$ wherein $R^4$ is other than hydrogen, azido and —$NHR^5$ wherein $R^5$ is other than hydrogen can be prepared by acylation procedures analogous to those used to esterify DMOT or 23-O-acyl-DMT. For esters of those C-23 derivatives wherein $R^4$ or $R^5$ is hydrogen, acylation of the hydroxyl groups is carried out on an intermediate (e.g. $R^4$ is acetyl or R is azido). The desired C-23 derivative is subsequently prepared by the appropriate modification of the 23-substituent (e.g. hydrolysis of —S-acetyl or reduction of the azide).

Alternatively, the esters of the C-23-modified derivatives of DMT can be prepared by starting with the corresponding ester derivatives of DMT, prepared as described in U.S. Pat. No. 4,321,361 and 4,321,362 and in Kirst application Serial No. 354,262. The 23-substituent of these esters of DMT can then be modified by the procedures described supra. It should also be noted that hydrolysis of such an ester derivative yields the corresponding C-23-modified derivative of DMT.

The DMT derivatives of this invention form acid addition salts. These acid addition salts are also useful as antibiotics and are a part of this invention. In another aspect, such salts are useful as intermediates, for example, for separating and purifying the DMT derivatives. In addition, the salts have an improved solubility in water.

Representative suitable salts include those salts formed by standard reactions with both organic and inorganic acids such as, for example, sulfuric, hydrochloric, phosphoric, acetic, succinic, citric, lactic, maleic, fumaric, palmitic, cholic, pamoic, mucic, D-glutamic, d-camphoric, glutaric, glycolic, phthalic, tartaric, formic, lauric, stearic, salicylic, methanesulfonic, benzenesulfonic, sorbic, picric, benzoic, cinnamic, and like acids. Pharmaceutically acceptable acid addition salts are an especially preferred group of salts.

Illustrative DMT derivatives of this invention include those compounds of formula 1 listed in Tables I and II.

TABLE I

Illustrative C-23 Modified Derivatives of DMT[a]

| Compound No. | R |
|---|---|
| 1 | azido |
| 2 | amino |
| 3 | N—(phenylacetyl)amino |
| 4 | phenylthio |
| 5 | iodo |
| 6 | bromo |
| 7 | chloro |
| 8 | fluoro |
| 9 | (1-methyltetrazol-5-yl)thio |
| 10 | (5-methyl-1,3,4-thiadiazol-2-yl)thio |
| 11 | (5-methyl-1,3,4-oxadiazol-2-yl)thio |
| 12 | acetylthio |
| 13 | (1,2,4-triazin-3-yl)thio |
| 14 | (1H-5,6-dioxo-4-methyl-1,2,4-triazin-3-yl)thio |
| 15 | 3,4-dichlorophenylthio |
| 16 | pyridinium |

[a]$R^1$, $R^2$, $R^3$ = H

TABLE II

Illustrative C-23-Modified Ester Derivatives of DMT

| R | $R^1$ (3) | $R^2$ (2') | $R^3$ (4'') |
|---|---|---|---|
| fluoro | H | H | isovaleryl |
| fluoro | acetyl | H | H |
| bromo | H | acetyl | H |
| chloro | acetyl | H | phenylacetyl |
| phenylthio | phenylacetyl | H | H |
| phenylthio | acetyl | H | isovaleryl |
| (1-methyltetrazol-2-yl)thio | acetyl | H | H |
| (1,3,4-thiadiazol-2-yl)thio | propionyl | H | p-nitrophenylacetyl |
| (1,3,4-oxadiazol-2-yl)thio | H | acetyl | H |

TABLE II-continued

Illustrative C-23-Modified Ester Derivatives of DMT

| R | $R^1$ (3) | $R^2$ (2') | $R^3$ (4'') |
|---|---|---|---|
| acetylthio | H | acetyl | n-butyryl |
| azido | H | propionyl | H |
| azido | acetyl | propionyl | acetyl |
| acetamido | H | propionyl | H |
| phenylacetamido | H | H | isovaleryl |
| phenylacetamido | acetyl | H | isovaleryl |
| phenylacetamido | acetyl | acetyl | acetyl |
| 3,4-dichlorophenylthio | phenoxyacetyl | H | H |

The DMT derivatives of this invention inhibit the growth of pathogenic bacteria, especially grampositive bacteria, Mycoplasma species and Pasteurella species. The minimal inhibitory concentrations (MIC's) at which illustrative compounds inhibit certain bacteria are given in Tables III and IV. The MIC's in Table III were determined by standard agar-dilution assays. The MIC's in Table IV were obtained using a conventional broth-dilution microtiter test.

TABLE III

Antibiotic Activity of C-23 Modified Derivatives of DMT[a]

| | Test Compound[b] | | | |
|---|---|---|---|---|
| Test Organism | 1 | 2 | 3 | 4 |
| Staphylococcus aureus X1.1 | 0.25 | 2 | 0.5 | 0.5 |
| Staphylococcus aureus V41[c] | 0.25 | 8 | 1 | 0.25 |
| Staphylococcus aureus X400[d] | 0.5 | 8 | 1 | 0.5 |
| Staphylococcus aureus S13E | 0.25 | 4 | 0.5 | 0.5 |
| Staphylococcus epidermidis EPI1 | 0.25 | 4 | 0.5 | 0.5 |
| Staphylococcus epidermidis EPI2 | 0.25 | 8 | 1 | 0.5 |
| Streptococcus pyogenes C203 | 0.125 | 1 | 0.25 | 0.125 |
| Streptococcus pneumoniae Park I | 0.06 | 0.5 | 0.25 | 0.03 |
| Streptococcus Group D X66 | 0.5 | 8 | 0.5 | 0.25 |
| Streptococcus Group 9960 | 0.25 | 8 | 0.5 | 0.125 |
| Haemophilus influenzae Holt[e] | 8 | 16 | 8 | 4 |
| Haemophilus influenzae R52[f] | 8 | 16 | 8 | NT[g] |

[a]MIC in mcg/ml
[b]Compound numbers from Table I
[c]Penicillin-resistant strain
[d]Methicillin-resistant strain
[e]Ampicillin-sensitive strain
[f]Ampicillin-resistant strain
[g]NT = no test

TABLE IV

Antibiotic Activity of DMT Derivatives[a]

| | Test Compound[b] | | | |
|---|---|---|---|---|
| Test Organism | 1 | 2 | 3 | 4 |
| Staphylococcus aureus | 1.56 | 6.25 | 1.56 | 0.39 |
| Streptococcus bovis 80 | 0.39 | 1.56 | 0.19 | 0.19 |
| Pasteurella multocida 17E[c] | 6.25 | 6.25 | 12.5 | 6.25 |
| Pasteurella multocida 60A[d] | 6.25 | 12.5 | 25 | 6.25 |
| Pasteurella multocida 22A | 12.5 | 12.5 | 50 | 12.5 |
| Pasteurella multocida 40G | 6.25 | 12.5 | 25 | 6.25 |
| Pasteurella multocida 68C | 6.25 | 12.5 | 25 | 12.5 |
| Pasteurella hemolytica 22C | 25 | 25 | 50 | 25 |
| Pasteurella hemolytica 41D | 25 | 12.5 | 25 | 12.5 |
| Pasteurella hemolytica 23C | 25 | 12.5 | 25 | 25 |
| Mycoplasma gallisepticum | 0.19 | 1.56 | 0.09 | ≦0.05 |
| Mycoplasma synoviae | 0.78 | 0.78 | 0.39 | 0.19 |
| Mycoplasma hyorhinis | ≧50 | 25 | 1.56 | 0.78 |

[a]MIC in mcg/ml
[b]Compound numbers from Table I
[c]Bovine isolate
[d]Avian isolate The C-23 modified derivatives of DMT of this invention have shown in vivo antimicrobial activity against experimentally-induced infections in laboratory animals. When two doses of test compound were administered to mice experimentally infected with *S. pyogenes* C203, the activity observed was measured as an $ED_{50}$ value [effective dose in mg/kg to protect 50% of the test animals: see Warren Wick, et al., *J. Bacteriol.* 81, 233-235 (1961)]. $ED_{50}$ values observed for illustrative compounds are given in Table V.

TABLE V

| ED$_{50}$ Values of DMT Derivatives[a] | | |
|---|---|---|
| | *Streptococcus pyogenes* C203 | |
| Test Compound[b] | Subcutaneous | Oral |
| 1 | 10.5 | 68 |
| 2 | <1.5 | >100 |
| 3 | 3.8 | >100 |
| 4 | <25 | 71 |

[a]mg/kg × 2; doses given 1 and 4 hours post-infection
[b]Compound numbers from Table I The compounds of this invention have also exhibited in vivo activity against experimental infections caused by *Mycoplasma gallisepticum*. In these tests infections were induced in chicks by injecting 0.2 ml. of a broth culture of *M. gallisepticum* into the abdominal air sac of two- to three-day-old chicks. The compounds were administered subcutaneously at a dose of 60 mg/kg once only on the day of infection or, at the same level, two times on the day of infection and two times on the first day post-infection. Twenty-one days post-infection, the chicks were weighed, a blood sample was taken, and the chicks were sacrificed. The presence or absence of air-sac lesions was recorded. The results of these tests are summarized in Table VI.

TABLE VI

| | | | Antimycoplasmal Activity of DMT Derivatives in Chicks | |
|---|---|---|---|---|
| | | | *Mycoplasma gallisepticum* | |
| Test Compound[a] | Dosage Level | Mortality | Number with Air-Sac Lesions/ Number Treated | Number with Antibodies[b] Number Tested |
| 1 | 60 mg/kg × 4 | 0/10 | 0/10 | 0/10 |
| | 60 mg/kg × 1 | 0/10 | 3/10 | 5/10 |
| 3 | 60 mg/kg × 4 | 0/10 | 0/10 | 3/10 |
| | 60 mg/kg × 1 | 1/10 | 8/10 | 8/9 |
| 4 | 60 mg/kg × 4 | 0/10 | 3/10 | 7/10 |
| | 60 mg/kg × 1 | 0/10 | 7/10 | 8/10 |
| Infected Control | 0 | 5/9 | 9/9 | 9/9 |
| Normal Control | 0 | 0/10 | 0/10 | 0/10 |

[a]Compound numbers from Table I
[b]Antibodies to *M. gallisepticum*

This invention also relates to methods of controlling bacterial or mycoplasmal infections. In carrying out the methods of this invention, an effective amount of a compound of formula 1 is administered parenterally or orally to an infected or susceptible warm-blooded animal. The compounds can also be administered by insufflation, i.e. by blowing the compound, in the form of a medicated dust, into an enclosed space or room wherein the animals or poultry are held. The animals or poultry breathe the medicated dust present in the air; the medicated dust is also taken into the body through the eyes (a process called intraocular injection).

The dose which is effective to control the infection will vary with the severity of the infection and the age, weight, and condition of the animal. The total dose required for protection parenterally will generally, however, be in the range of from about 1 to about 100 mg/kg and preferably will be in the range of from about 1 to about 50 mg/kg. The dose required for oral administration will generally be in the range of from 1 to about 300 mg/kg and preferably will be in the range of from about 1 to about 100 mg/kg. Suitable dosage regimens can be constructed.

Often the most practical way to administer the compounds is by formulation into the feed supply or drinking water. A variety of feeds, including the common dry feeds, liquid feeds, and pelleted feeds, may be used.

In another aspect, this invention relates to compositions useful for the control of gram-positive bacterial, Pasteurella and Mycoplasma infections. These compositions comprise a compound of formula 1 together with a suitable vehicle. Compositions may be formulated for parenteral or oral administration by methods recognized in the pharmaceutical art.

The methods of formulating drugs into animal feeds are well-known. A preferred method is to make a concentrated-drug premix which in turn is used to prepare medicated feeds. Typical premixes may contain from about 1 to about 200 grams of drug per pound of premix. Premixes may be either liquid or solid preparations.

The final formulation of feeds for animals or poultry will depend upon the amount of drug to be administered. The common methods of formulating, mixing, and pelleting feeds may be used to prepare feeds containing a compound of formula 1.

Effective injectable compositions containing these compounds may be in either suspension or solution form. In the preparation of suitable formulations it will be recognized that, in general, the water solubility of the acid addition salts is greater than that of the free bases. Similarly, the bases are more soluble in dilute acids or in acidic solutions than in neutral or basic solutions.

In the solution form the compound is dissolved in a physiologically acceptable vehicle. Such vehicles comprise a suitable solvent, preservatives such as benzyl alcohol, if needed, and buffers. Useful solvents include, for example, water and aqueous alcohols, glycols, and carbonate esters such as diethyl carbonate. Such aqueous solutions contain, in general, no more than 50% of the organic solvent by volume.

Injectable suspension compositions require a liquid suspending medium, with or without adjuvants, as a vehicle. The suspending medium can be, for example, aqueous polyvinylpyrrolidone, inert oils such as vegetable oils or highly refined mineral oils, or aqueous carboxymethylcellulose.

Suitable physiologically acceptable adjuvants are necessary to keep the compound suspended in suspension compositions. The adjuvants may be chosen from among thickeners such as carboxymethylcellulose, polyvinylpyrrolidone, gelatin, and the alginates. Many surfactants are also useful as suspending agents. Lecithin, alkyphenol polyethylene oxide adducts, naphthalenesulfonates, alkylbenzenesulfonates, and the polyoxyethylene sorbitan esters are useful suspending agents.

Many substances which affect the hydrophilicity, density, and surface tension of the liquid suspending medium can assist in making injectable suspensions in individual cases. For example, silicone antifoams, sorbitol, and sugars can be useful suspending agents.

In order to illustrate more fully the operation of this invention, the following examples are provided:

EXAMPLE 1

23-Deoxy-23-Azido-DMT

A solution of DMT (15.0 g, 20.2 mmol) and s-collidine (5.8 ml, 43.7 mmole) in dichloromethane (250 ml) was cooled to −78° C. under argon and treated dropwise with trifluoromethanesulfonic anhydride (5.8 ml, 34.5 mmole) and then with lithium azide (2.975 g, 60.7 mmole). The cooling bath was removed, and after thirty minutes the reaction mixture was diluted with acetonitrile to bring the lithium azide into solution. After two hours the reaction mixture was evaporated to dryness, and the residue was dissolved in dichloromethane. This solution was extracted with saturated sodium bicarbonate solution, dried over sodium sulfate, filtered and evaporated. The crude product thus obtained was purified by silica-gel chromatography (Waters Prep 500), eluting with a linear gradient of 4 L of dichloromethane and 4 L of methanol/dichloromethane (3:22) to give 10.37 g (67%) of 23-deoxy-23-azido-DMT.

EXAMPLE 2

23-Deoxy-23-amino-DMT

A solution of 23-deoxy-23-azido-DMT (7.98 g, 10.4 mmole) prepared as described in Example 1, triphenylphosphine (2.86 g, 10.9 mmole) and water (0.25 ml, 13.9 mmole) in distilled tetrahydrofuran (200 ml) was stirred at room temperature for four days. The reaction mixture was evaporated to give a glassy solid which was partitioned between ethyl acetate and 0.1 M acetic acid solution. The aqueous layer was separated, washed with ethyl acetate and carefully poured into saturated sodium bicarbonate solution. The resulting mixture was extracted with dichloromethane, dried over sodium sulfate, filtered and evaporated to give 7.5 g (97.5%) of 23-deoxy-23-amino-DMT.

EXAMPLE 3

23-Deoxy-23-(phenylacetyl)amino-DMT

A solution of 23-deoxy-23-amino-DMT (1.48 g, 2.0 mmole) in 10% aqueous acetone (50 ml) was treated with N-(phenylacetyl)oxysuccinimide (446 mg, 2.0 mmole) and stirred at room temperature for two hours. After the addition of a few drops of methanol, the reaction mixture was evaporated to an aqueous solution which was extracted with dichloromethane. The organic layer was separated and extracted with saturated sodium bicarbonate solution, dried over sodium sulfate, filtered, and evaporated. The residual glassy solid was purified by silica-gel flash chromatography, eluting with a linear gradient of 750 ml dichloromethane and 750 ml of methanol/dichloromethane (1:4) to give 1.07 g (62%) of 23-deoxy-23-(phenylacetyl)amino-DMT.

EXAMPLE 4

23-Deoxy-23-(phenyl)thio-DMT

A solution of DMT (10.0 g, 13.5 mmole) and s-collidine (3.6 ml, 27.3 mmole) in dichloromethane (200 ml) was cooled to −78° C. under argon and treated dropwise with trifluoromethanesulfonic anhydride (3.4 ml, 20.2 mmole). Ten minutes after the addition was completed, the reaction mixture was warmed to −25° C., and thiophenol (2.08 ml, 20.2 mmole) was added. The cooling bath was removed, and the reaction was allowed to come to room temperature over a one-hour period. The reaction solution was extracted with saturated sodium bicarbonate solution, dried over sodium sulfate, filtered and evaporated. The residue was dissolved in cyclohexane and again evaporated to give a crude product. This product was purified by silica-gel chromatography (Waters Prep 500), eluting with a linear gradient of 4 L of dichloromethane and 4 L of methanol/dichloromethane (5:95) to give 1.4 g (12.5%) of 23-deoxy-23-(phenyl)thio-DMT.

EXAMPLE 5

Injectable Formulations (A) A formula 1 base is added to propylene glycol. Water and benzyl alcohol are added so that the solutions contains 50% (by volume) propylene glycol, 4% (by volume) benzyl alcohol, and 200 mg/ml of a formula 1 base.

(B) A solution is prepared as described in Section A except that the solution contains 50 mg/ml of a formula 1 base.

(C) A solution is prepared as described in Section A except that the solution contains 350 mg/ml of a formula 1 base.

(D) A solution is prepared as described in Section A except that the solution contains 500 mg/ml of a formula 1 tartrate.

(E) A suspension is prepared by adding a finely ground formula 1 compound to carboxymethyl cellulose with thorough mixing so that the suspension contains 200 mg of the formula 1 base per ml of suspension.

EXAMPLE 6

Chick Ration for Control of Mycoplasma

A balanced, high-energy ration adapted to feed chicks for rapid weight gain is prepared by the following recipe:

| Ingredient | % | lbs |
| --- | --- | --- |
| Ground yellow corn | 50 | 1,000 |
| Soybean meal, solvent-extracted dehulled, finely ground, 50 percent protein | 31.09 | 621.8 |
| Animal fat (beef tallow) | 6.5 | 130 |
| Dried fish meal, with solubles (60% protein) | 5.0 | 100 |
| Distillers' solubles from corn | 4.0 | 80 |
| Dicalcium phosphate, feed grade | 1.8 | 36 |
| Calcium carbonate | 0.8 | 16 |
| Vitamin premix (representing vitamins A, D, E, K, and $B_{12}$, choline, niacin, pantothenic acid, riboflavin, biotin, with glucose bulking agent) | 0.5 | 10 |
| Trace mineral premix | 0.2 | 4 |

| Ingredient | % | lbs |
|---|---|---|
| (representing MnSO4, ZnO, KI, FeSO4, CaCO3) | | |
| 2-Amino-4-hydroxybutyric acid (hydroxy analog of methionine) | 0.1 | 2 |
| Formula 1 compound | 0.01 | 0.2 |

These substances are mixed in accordance with standard feed-mixing techniques. Chicks fed such a ration, with water ad libitum, are protected against exposure to mycoplasmal infections.

We claim:

1. A compound of formula 1

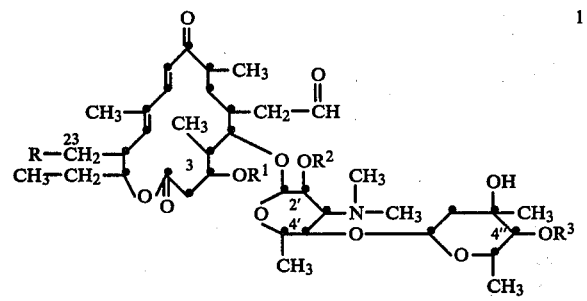

wherein
R is iodo, bromo, chloro, fluoro, —S—R$^4$, azido, —NHR$^5$, pyridinium or —OSO$_2$CF$_3$;
R$^1$ is hydrogen, C$_1$-C$_5$-alkanoyl or C$_1$-C$_5$-alkanoyl having from one to three halo substituents; benzoyl, phenylacetyl, phenylpropionyl, phenoxyacetyl or phenylthioacetyl; or benzoyl, phenylacetyl, phenylpropionyl, phenoxyacetyl or phenylthioacetyl having from one to five halo or methyl groups or from one to two methoxyl, nitro or hydroxyl groups;
R$^2$ is hydrogen, C$_1$-C$_5$-alkanoyl or C$_1$-C$_5$-alkanoyl having from one to three halo substituents; benzoyl, phenylacetyl or phenylpropionyl; or benzoyl, phenylacetyl, or phenylpropionyl having from one to five halo or methyl groups or from one to two methoxyl, nitro or hydroxyl groups;
R$^3$ is hydrogen, C$_1$-C$_5$-alkanoyl or C$_1$-C$_5$-alkanoyl having from one to three halo substituents; benzoyl, phenylacetyl or phenoxyacetyl; or benzoyl, phenylacetyl or phenoxyacetyl having from one to five halo or methyl groups or from one to two methoxyl, nitro or hydroxyl groups;
R$^4$ is hydrogen, C$_1$-C$_6$ alkyl, cyclohexyl, C$_1$-C$_5$-alkanoyl, phenyl or benzyl; phenyl or benzyl having from one to five halo or methyl groups or from one to two methoxyl, nitro or hydroxyl groups; a heteroaryl group selected from imidazolyl, pyrazolyl, pyridyl, pyrimidyl, pyrazinyl, pyridazinyl, triazinyl, triazolyl, tetrazolyl, oxazolyl, isoxazolyl, oxadiazolyl, thiazolyl, isothiazolyl, thiadoiazolyl, thienyl and furanyl; or a specified heteroaryl group having a C$_1$-C$_4$-alkyl, methoxy, ethoxy, hydroxy, keto, phenyl, halophenyl, methylphenyl, or methoxyphenyl substituent; and
R$^5$ is hydrogen or an acyl group selected from C$_1$-C$_5$- alkanoly or C$_1$=C$_5$-alkanoyl having from one to three halo substituents; benzoyl, phenylacetyl or phenylpropionyl; or benzoyl, phenylacetyl or phenylpropionyl having from one to five halo or methyl group or from one to two methoxyl, nitro or hydroxyl groups;
and the acid addition salts thereof.

2. A compound of claim 1 wherein R is iodo.
3. A compound of claim 1 wherein R is bromo.
4. A compound of claim 1 wherein R is chloro.
5. A compound of claim 1 wherein R is fluoro.
6. A compound of claim 1 wherein R is —S—R$^4$.
7. A compound of claim 6 wherein R$^4$ is phenyl or phenyl having from one to five halo or methyl groups or from one to two methoxyl, nitro or hydroxyl groups.
8. A compound of claim 7 wherein R$^4$ is phenyl.
9. A compound of claim 6 wherein R$^4$ is a specified heteroaryl group or a specified heteroaryl group having a C$_1$-C$_4$-alkyl, methoxy, ethoxy, hydroxy, keto, phenyl, halophenyl, methylphenyl, or methoxyphenyl substituent.
10. A compound of claim 9 wherein R$^4$ is tetrazolyl.
11. A compound of claim 10 wherein R$^4$ is 1-methyltetrazol-2-yl.
12. A compound of claim 9 wherein R$^4$ is thiadiazolyl.
13. A compound of claim 12 wherein R$^4$ is 5-methyl-1,3,4-thiadiazol-2-yl.
14. A compound of claim 9 wherein R$^4$ is oxadiazolyl.
15. A compound of claim 14 wherein R$^4$ is 5-methyl-1,3,4-oxadiazol-2-yl.
16. A compound of claim 9 wherein R$^4$ is triazinyl.
17. A compound of claim 16 wherein R$^4$ is 1,2,4-triazin-3-yl.
18. A compound of claim 16 wherein R$^4$ is 1H-5,6-dioxo-4-methyl-1,2,4-triazin-3-yl.
19. A compound of claim 6 wherein R$^4$ is C$_1$-C$_5$-alkanoyl.
20. A compound of claim 1 wherein R is azido.
21. A compound of claim 1 wherein R is —NHR$^5$.
22. A compound of claim 21 wherein R$^5$ is hydrogen.
23. A compound of claim 21 wherein R$^5$ is C$_1$-C$_5$-alkanoyl or C$_1$-C$_5$-alkanoyl having from one to three halo substituents.
24. A compound of claim 23 wherein R$^5$ is acetyl.
25. A compound of claim 21 wherein R$^5$ is benzoyl, phenylacetyl, or phenylpropionyl or benzoyl, phenylacetyl or phenylpropionyl having from one to five halo or methyl groups or from one to two methoxyl, nitro or hydroxyl groups.
26. A compound of claim 25 wherein R$^5$ is phenylacetyl.
27. A compound of claim 1 wherein R is —OSO$_2$CF$_3$.
28. A compound of claim 1, 2, 3, 4, 5, 6, 9, 20, 21 or 27 wherein R$^1$, R$^2$, and R$^3$ are hydrogen.
29. A compound of claim 1, 2, 3, 4, 5, 6, 9, 20, 21 or 27 wherein R$^3$ is C$_1$-C$_5$-alkanoyl or C$_1$-C$_5$-alkanoyl having from one to three halo substituents.
30. A compound of claim 29 wherein R$^3$ is isovaleryl or butyryl.
31. A compound of claim 1, 2, 3, 4, 5, 6, 9, 20, 21 or 27 wherein R$^1$ is benzoyl, phenylacetyl, phenylpropionyl, phenoxyacetyl or phenylthioacetyl or benzoyl, phenylacetyl, phenylpropionyl, phenoxyacetyl or phenylthioacetyl having from one to five halo or methyl groups or from one to two methoxyl, nitro or hydroxyl groups.
32. A compound of claim 31 wherein R$^1$ is phenylacetyl.

33. A method for treating mycoplasmal infections which comprises administering to an infected or susceptible warm-blooded animal an effective amount of a compound of claim 1, 2, 3, 4, 5, 6, 9, 20 or 21 or a pharmaceutically-acceptable acid addition salt thereof and a suitable pharmaceutical vehicle.

34. A method for treating gram-positive infections which comprises administering to an infected or susceptible warm-blooded animal an effective amount of a composition comprising a compound of claim 1, 2, 3, 4, 5, 6, 20 or 21 or a pharmaceutically-acceptable acid addition salt thereof and a suitable pharmaceutical vehicle.

35. A composition useful for the treatment of gram-positive, Pasteurella or Mycoplasma infections comprising an effective amount of a compound of claim 1 or a pharmaceutically acceptable acid addition salt thereof and a suitable pharmaceutical vehicle.

* * * * *

UNITED STATES PATENT AND TRADEMARK OFFICE
CERTIFICATE OF CORRECTION

PATENT NO. : 4,452,784
DATED : June 5, 1984
INVENTOR(S) : Herbert A. Kirst and John E. Toth It is certified that error appears in the above—identified patent and that said Letters Patent is hereby corrected as shown below:

Column 6, line 36, "Haemophilus influenzae $R52^f$" should read --Haemophilus influenzae $R252^f$--.

Column 7, line 12, "<25" should read -->25--.

Column 7, lines 52-53, "aminal" should read --animal--.

Column 11, line 60, "thiadoiazolyl," should read --thiadiazolyl,--.

Column 11, line 66, "alkanoly" should read --alkanoyl--.

Column 12, line 2 "group" should read --groups--.

Column 14, line 1 "5, 6, 20 or 21" should read --5, 6, 9, 20 or 21--.

Signed and Sealed this

Ninth Day of April 1985

[SEAL]

Attest:

DONALD J. QUIGG

Attesting Officer     Acting Commissioner of Patents and Trademarks